(12) United States Patent
Lindner et al.

(10) Patent No.: US 11,123,123 B2
(45) Date of Patent: Sep. 21, 2021

(54) MEDICAL BONE SCREW AND IMPLANT SYSTEM

(71) Applicant: Aesculap AG, Tuttlingen (DE)

(72) Inventors: Stephan Lindner, Wurmlingen (DE); Jens Schneider, Radolfzell (DE)

(73) Assignee: AESCULAP AG, Tuttlingen (DE)

(*) Notice: Subject to any disclaimer, the term of this patent is extended or adjusted under 35 U.S.C. 154(b) by 0 days.

(21) Appl. No.: 16/963,692

(22) PCT Filed: Jan. 25, 2019

(86) PCT No.: PCT/EP2019/051880
§ 371 (c)(1),
(2) Date: Jul. 21, 2020

(87) PCT Pub. No.: WO2019/145490
PCT Pub. Date: Aug. 1, 2019

(65) Prior Publication Data
US 2021/0244454 A1  Aug. 12, 2021

(30) Foreign Application Priority Data

Jan. 25, 2018 (DE) .......................... 102018101657.3

(51) Int. Cl.
*A61B 17/86* (2006.01)
*A61F 2/34* (2006.01)
*A61F 2/30* (2006.01)

(52) U.S. Cl.
CPC ...... *A61B 17/8605* (2013.01); *A61B 17/8625* (2013.01); *A61F 2/30749* (2013.01); *A61F 2/34* (2013.01); *A61F 2002/3406* (2013.01)

(58) Field of Classification Search
CPC ............. A61B 17/8605; A61B 17/8033; A61F 2002/3406; A61F 2/34
See application file for complete search history.

(56) References Cited

U.S. PATENT DOCUMENTS

| | | | |
|---|---|---|---|
| 4,955,919 A | 9/1990 | Pappas et al. | |
| 5,571,198 A | 11/1996 | Drucker et al. | |
| 5,725,588 A | 3/1998 | Errico et al. | |
| 6,213,775 B1 | 4/2001 | Reipur | |
| 9,044,277 B2 * | 6/2015 | O'Neil ............... A61B 17/7064 | |

(Continued)

FOREIGN PATENT DOCUMENTS

| | | |
|---|---|---|
| CN | 1249673 A | 4/2000 |
| CN | 101917936 A | 12/2010 |

(Continued)

OTHER PUBLICATIONS

Office Action received in Japanese Application No. 2020-560593 dated Apr. 30, 2021, with translation, 6 pages.

(Continued)

*Primary Examiner* — Andrew Yang

(57) ABSTRACT

An implant system includes an acetabular implant and a bone screw having an articulated screw head which allows an unchanged contact position of the screw head on the acetabular implant when the bone screw is aligned relative to the acetabular implant. For this purpose, a slotted hole is made in the acetabular implant in which slotted hole the bone screw can be pivoted in longitudinal direction of the slotted hole.

13 Claims, 4 Drawing Sheets

(56) References Cited

U.S. PATENT DOCUMENTS

| | | | |
|---|---|---|---|
| 9,179,953 B2 * | 11/2015 | Weiman | A61B 17/86 |
| 9,655,665 B2 | 5/2017 | Perrow | |
| 9,662,145 B2 | 5/2017 | Harris et al. | |
| 2004/0068319 A1 | 4/2004 | Cordaro | |
| 2006/0190090 A1 | 8/2006 | Plaskon | |
| 2014/0100572 A1 | 4/2014 | Biedermann | |
| 2014/0324108 A1 | 10/2014 | Orbay et al. | |

FOREIGN PATENT DOCUMENTS

| | | |
|---|---|---|
| DE | 9110508 U1 | 10/1991 |
| EP | 1068843 A1 | 1/2001 |
| JP | H11503351 A | 3/1999 |
| WO | 9632071 A1 | 10/1996 |
| WO | 2004082493 A1 | 9/2004 |
| WO | 2009081346 A1 | 7/2009 |

OTHER PUBLICATIONS

German Search Report received in Application No. 10 2018 101 657.3, dated Dec. 6, 2018, 14 pags. (with translation).

International Search Report received in International Application No. PCT/EP2019/051880, dated May 16, 2019, 13 pages.

International Preliminary Report and Written Opinion received in International Application No. PCT/EP2019/051880, dated May 16, 2019, 23 pages.

Office Action received in Chinese Application No. 201980008730.7 dated Mar. 31, 2021, with translation, 20 pages.

* cited by examiner

MEDICAL BONE SCREW AND IMPLANT SYSTEM

CROSS-REFERENCE TO RELATED APPLICATIONS

This application is the United States national phase entry of International Application No. PCT/EP2019/051880, filed Jan. 25, 2019, and claims the benefit of priority of German Application No. 10 2018 101 657.3, filed Jan. 25, 2018. The contents of International Application No. PCT/EP2019/051880 and German Application No. 10 2018 101 657.3 are incorporated by reference herein in their entireties.

FIELD

The invention relates to an implant system having at least one medical bone screw and a hip-joint acetabular implant, which has at least one clearance hole through which the medical bone screw can be inserted in such a way that the medical bone screw can be pivoted at least in one direction of the clearance hole.

BACKGROUND

For anchoring hip joint acetabular implants/artificial hip-joint acetabula in the pelvic bone, the hip-joint acetabular implants to be implanted are often fixed with bone screws, in particular during revision procedures or primary severe destruction of the hip joint on the pelvic side. In order to enable stable anchoring of the bone screws in the pelvic bone, the bone screws have to be placed at a location in the pelvic bone where there is enough and sufficiently load-bearing bone. In order to enable the placement of the bone screws at such a location when screwing the hip joint acetabular implant to the hip bone, the bone screw needs the highest possible degree of freedom with regard to the bone-screw entry point in the bone as well as the angulation/angle of the screw axis in relation to the outer geometry or the normal vector of the outer geometry of the hip joint acetabular implant.

In the case of thin-walled hip-joint acetabular implants, however, even a slight inclination of the bone screw in the intended hole of the hip-joint acetabular implant can result in the bone-screw head protruding into the interior of the hip-joint acetabular implant due to the angulation and thus an inlay that is to be brought into contact there rests on the bone-screw head, which prevents stable anchoring of the inlay in the hip-joint acetabular implant and which may lead to early implant failure.

Furthermore, there is a risk of screwing through at the junction of the bone screw and the hip-joint acetabular implant when tightening the bone screw, so that this junction has to be designed to be robust. In addition, when tightening the bone screw, the screwdriver can become jammed due to deformation of the bone-screw head, and the bone screw might unintentionally be torn out of the bone structure or the screwdriver might be difficult to reinsert.

The prior art shows a hip-joint acetabular implant, which allows the bone screw more angular play due to special screw holes, which protrude on the outside of the hip joint acetabular implant and have conical bores of round cross-section. The production of such a hip-joint acetabular implant is, however, on the one hand complex due to the protruding screw hole and entails increased effort in the surgical technique, and on the other hand the bone-screw entry point can only be placed within the pivot circle around the center of the round bore.

An implant system is known from patent specification U.S. Pat. No. 9,655,665 B2, which provides a washer with a round cross-section for a bone screw, which has two pins on the outside of its circumferential edge, on which the washer can be rotatably supported in a complementarily designed recess of the implant. The support positions of the pins in the implant are defined so that a bone screw screwed onto this washer can only be positioned within a radius around the rotational axis of the washer.

U.S. Pat. No. 9,662,145 B2 shows an implant system with a bone screw and a non-circular washer for a slotted hole, with which the bone screw can be secured against being screwed through, but which cannot prevent the screw head from protruding into the interior of the implant when the bone screw is tilted.

SUMMARY

It is therefore the object of the invention to eliminate or at least reduce the disadvantages of the prior art. In particular, when screwing a hip-joint acetabular implant to a patient's bone, it should be possible to select the overall position or the arrangement of the bone screw in the bone as freely as possible, i.e. the bone-screw entry point as well as the angulation of the bone screw with respect to the outer geometry of the hip-joint acetabular implant, in order to offer an ideal hold in the bone for the bone screw. In particular, it is intended to prevent or at least reduce the risk of a hip-joint acetabular implant inlay resting on the head of a bone screw angled with respect to the outer geometry of the hip joint acetabular implant and also to prevent the bone screw from being screwed through at the junction between the hip joint acetabular implant and the bone screw. In addition, in particular jamming of the screwdriver in the head of the bone screw is to be prevented when tightening the bone screw.

A basic idea of the invention is to create a bone screw with an articulated head for screwing the hip-joint acetabular implant to the patient's bone, which gives the bone-screw shaft of the bone screw at least one additional degree of freedom in its orientation relative to the hip-joint acetabular implant and/or allows an unchanged contact position of the screw head on the hip-joint acetabular implant when the bone-screw shaft is angled relative to the hip joint acetabular implant. In the hip joint acetabular implant, at least one clearance hole, preferably a slotted hole, preferably two or more slotted holes, is/are provided, into which the bone screw can be inserted in such a way that the bone screw can be pivoted in at least one direction of the clearance hole, preferably can be freely placed along the longitudinal axis of the slotted hole and can be pivoted in the direction of the longitudinal axis.

Specifically, an implant system is proposed having at least one medical bone screw and a hip-joint acetabular implant, which has at least one clearance hole, preferably a slotted hole with two opposite, long longitudinal sides and two opposite, short transverse sides, and through which the medical bone screw can be inserted in such a way that the medical bone screw can be pivoted at least in one direction of the clearance hole, preferably at least in the longitudinal direction of the slotted hole, especially preferably in the longitudinal and transverse direction of the clearance hole. The medical bone screw has a shaft-shaped bone thread part for fixing the hip-joint acetabular implant to a patient's bone, which has a core diameter (e.g. 3 mm) and an outer-thread diameter (e.g. 6.5 mm) and at the proximal end of which a two-part, angle-adjustable head part is attached. Furthermore, the two-part, angle-adjustable head part is formed of a head piece, which is preferably rotationally symmetrical, more preferably partially spherical or completely spherical, formed in one piece (of material) with the bone-thread part and a head piece, which is preferably not rotationally symmetrical, provided separately from the bone-thread part. The head piece provided separately from the bone-thread part has an upper side and a lower side and a clearance hole is introduced into it which has an undercut or a funnel shape or tulip shape. The clearance hole furthermore has a proximal clearance-hole diameter at the upper side, a distal clearance-hole diameter (e.g. 4.2 mm) at the lower side and between the upper side and the lower side it has an inner thread corresponding to the outer thread of the shaft-shaped bone thread part with an inner-thread diameter, wherein the inner-thread diameter is larger than the outer-thread diameter and the distal clearance-hole diameter is larger than the core diameter. Furthermore, the shaft-shaped bone thread part is inserted into the head piece provided separately from the bone-thread part, in particular by screwing the shaft-shaped bone thread part into the clearance hole, in such a way that the head piece formed in one piece (of material) therewith rests in an axially fixed manner at the undercut or respectively in the funnel shape or tulip shape, while a pivoting movement of the shaft-shaped bone thread part with respect to the separate head piece is allowed in at least one or exclusively one pivoting plane.

The opening or the inner circumferential side/circumferential surface of the funnel shape of the clearance hole can assume a linear and/or convex course in the axial direction of the clearance hole (in the direction of passage of the thread part through the clearance hole) or the diameter (of the funnel shape) of the clearance hole can taper linearly and/or exponentially (convexly) in the axial direction of the clearance hole.

In other words, for screwing a hip-joint acetabular implant to a patient's bone, a bone screw with a head part is provided, which consists of two subunits, which form an articulated connection in the assembled state, in particular in the manner of a ball joint, and which allow the threaded shaft part arranged distally to the head part a rotational movement relative to the head part in at least one plane, in particular in the manner of a ball joint. The first subunit of the head part is fixedly connected to the threaded shaft part, preferably connected in one piece and especially preferably connected in one piece of material/integrally, and in particular designed in the manner of a joint head. The second subunit of the head part has an aperture with an inner geometry which is (partially) complementary to the outer geometry of the first subunit in such a way that the second subunit at least partially encloses the first subunit in the assembled state and enters an articulated connection with the latter. For the assembly of the two subunits, the threaded shaft part of the bone screw is passed through the aperture of the second subunit so that the first subunit comes into contact at its outer circumference with the second subunit at its inner circumference. In particular the second subunit is formed in the manner of an joint socket/ball socket.

As an alternative to the inner thread, similar configurations of the inner circumferential surface of the clearance hole are conceivable, in which the circumferential surface of the clearance hole has (a) profiled recess(es) which is/are complementary to the outer profile of the shaft-shaped part of the bone screw, and by means of which the shaft-shaped part of the bone screw can be inserted. For example, the clearance hole may have a labyrinth on its circumference.

Due to the thread or the profiled recess(es), only intended movements of the separate head piece are possible along the bone-thread part or shaft-shaped part of the bone screw in the screw-in or insertion direction, whereas unintentional sliding/slipping/moving of the separate head piece along the thread part cannot occur.

It should be noted that in the context of this patent application the term 'proximal' always means an end or portion facing the user (surgeon) or facing away from the patient and, correspondingly, the term 'distal' means an end or portion facing away from the user or facing the patient.

By means of such a two-part head part of a bone screw, it is advantageously achieved that the head part can assume/be arranged in a fixed position in relation to its surroundings, in the present case at/in the clearance hole (slotted hole) of the hip joint acetabular implant (hereinafter referred to as implant), while the shaft-shaped bone thread part (hereinafter referred to as thread part) can be moved in relation to its surroundings, for example the outer geometry of the implant. It is thereby possible to determine the contact position of the head part at/in the implant exactly and still allow the thread part to have a variety of orientation possibilities.

In addition, the slotted hole advantageously offers along its longitudinal axis a variety of positioning possibilities for the head part of the screw or the thread part of the bone screw, which can be additionally angled by the articulated head part of the bone screw. Thus, on the one hand the bone-screw entry point into the patient's bone and on the other hand the angle of extension of the bone screw relative to the outer geometry of the implant (normal vector of the outer geometry) into the patient's bone can be freely selected.

Preferably, the head piece (hereinafter referred to as connected head piece), which is formed in one piece (of material) with the thread part, has an outer diameter of the head piece and the clearance hole has an intermediate clearance-hole diameter between the upper side and the lower side which is larger than, equal to, or smaller than the outer diameter of the head piece. In other words, the connected head piece and the separate head piece can be in a clearance fit or a press fit with each other in the assembled state of the head part. The intermediate clearance-hole diameter is the largest diameter in a central portion of the clearance hole located between a proximal portion of the clearance hole having the proximal clearance-hole diameter and a distal portion of the clearance hole having the distal clearance-hole diameter.

It is also conceivable that the separate head piece and the connected head piece form a (light) press fit. In particular, the proximal clearance-hole diameter is smaller than the outer diameter of the head piece. The assembly of the separate head piece on the connected head piece can be performed by snapping the separate head piece onto it. This ensures that the separate head piece is secured against loss or is held in a loss-preventing manner on the connected head piece or the thread part.

Furthermore, in the case of a provided press fit, it is possible that the separate head piece is heated so that the clearance hole widens to a diameter through which the (cooled) thread part can be inserted. After the separate head piece has cooled down, i.e. after the diameter of the clearance hole has narrowed, the thread part can no longer be pulled out of the separate head piece.

It is also conceivable that the thread part and the head piece connected to it are not joined together until assembly with the separate head piece. In concrete terms, this means that the separate head piece and the head piece to be connected to the thread part (in one piece) are first pre-assembled so that they assume their assembly position relative to each other. The thread part is then attached to the head piece to be connected, while the separate head piece is already in contact with the head piece to be connected and is thus held movably between the thread part and the connected head piece. In the same way, the thread part can be pre-assembled with the separate head piece and the head piece to be connected can then be added to the thread part. The connection of the thread part to the connected head piece can be achieved by welding, for example.

Preferably, the proximal clearance-hole diameter is larger than the distal clearance-hole diameter and/or the undercut or funnel shape or tulip shape of the clearance hole is designed and/or oriented in such a way that inevitably (only) one insertion direction of the thread part, i.e. from the upper side, results.

Specifically, the insertion direction can be determined in that the clearance hole has a diameter (only) on the upper side of the separate head piece that is sufficiently large to allow also the connected head piece to pass partially or completely through when the thread part is inserted/passed through the clearance hole (on the upper side).

The clarity/obviousness or the exclusivity of the insertion direction advantageously facilitates the assembly of the two head pieces for forming one head part and prevents incorrect joining of the two head pieces.

In addition, preferably the separate head piece has an essentially elliptical shape in top view with two opposite end portions with small radii and two opposite longitudinal portions with large radii, which are formed as parallel straight lines at least in longitudinal sections. Alternatively, the head piece can also take on an ellipse-like shape in top view with two opposite radial end portions and two opposite completely straight, parallel longitudinal portions.

Due to the longitudinal portions with large radii in top view, which are formed as parallel straight lines at least in longitudinal sections, or the completely straight, parallel longitudinal portions, the head part of the bone screw or the separate head piece can, in contrast to a completely round design in plan view, make line contact with its surroundings (the slotted hole or the implant) and assume a more stable contact position.

The top view is to be understood as a view onto the upper side in the axial direction of the clearance hole in the separate head piece.

In addition, preferably the separate head piece essentially has the form of a plano-convex lens and the upper side is planar. The outer shape of this plano-convex lens can also be described as a longitudinally bisected ellipsoid and/or as a longitudinally bisected, uniform egg. A walnut half also resembles this shape.

In particular, the separate, non-rotationally symmetric head piece, which is shaped as a substantially plano-convex lens, has a (lower side in the form of a) flattening on its convex side, which is oriented substantially plane-parallel to the planar upper side. This advantageously creates a support or contact surface that offers a larger support or contact surface to the separate head piece or head part in its surroundings.

In particular preferably, the bone screw has a threadless shaft portion axially between the outer thread of the thread part and the connected head piece, which is dimensioned in such a way that the outer thread of the thread part and the inner thread of the separate head piece are out of engagement when the connected head piece is axially fixed to the undercut or in the funnel shape or tulip shape.

The threadless shaft portion preferably has a diameter of 3 mm, in particular preferably it has the same diameter as the core thread of the thread part and especially preferably a diameter larger than 3 mm and smaller than the distal clearance-hole diameter.

This ensures that the separate head piece is or remains movable relative to the connected head piece in the axial contact position and ensures a joint-like connection at the head part of the bone screw in the assembly position.

Preferably, the separate head piece makes a linear and/or surface support contact with the implant along the two opposite longitudinal portions with large radii or being parallel in plan view. The enlarged support or contact surface secures the bone screw against screwing through. In addition, (elastic) deformation of the screw head during tightening of the bone screw is prevented or at least reduced by the larger abutment contact on the two longitudinal portions with large radii or being parallel in plan view. The risk of the screwdriver jamming in the, possibly, deformed screw head is thus reduced.

The separate head piece can also make a linear and/or surface supporting contact with the implant at one of the two opposite end portions with small radii and thus increase the supporting or abutting contact of the bone screw on the implant.

Furthermore preferably, the two opposite outer surfaces/outsides of the separate head piece, which connect the end portions with small radii of the (plane) upper side (where the thread part is inserted) with the lower side, show a convex course (towards the center of the separate head piece). It can also be said that these outer surfaces each take the shape of a convex runner or rocker. Along these rocker-like runners, the head part of the bone screw can be inclined further with respect to the implant. The orientation of the bone screw thus has even more placement flexibility.

In addition, the convex surface can be used advantageously as an enlarged contact surface for contacting the head part with the implant. It is in particular advantageous if the outer surface of the separate head piece, on its transverse sides (or on at least one transverse side), i.e. the surfaces connecting the end portions with small radii of the (planar) upper side with the lower side, are complementary to at least one transverse side of the slotted hole or the inner circumferential surface of a transverse side of the slotted hole. This advantageously further increases the surface support contact and stabilizes the contact of the head part at the implant.

Especially preferably, a circumferential contact surface or a circumferential projection is formed on the inner circumference or on the inner circumferential side of the clearance hole or slotted hole on the implant side, respectively, on which the separate head piece is supported in such a way that the separate head piece and/or the connected head piece in its contact position on/in the implant (hole) does not project axially beyond the inner circumferential edge of the clearance hole or slotted hole (the circumferential edge facing away from the patient bone and/or facing an inlay). In other words, the clearance hole or slotted hole may have a raised edge which, in the direction of its circumferential edge facing the patient's bone, has a circumferential contact surface (projecting into the clearance hole or slotted hole) for the separate head piece, substantially perpendicular to the inner circumferential side of the clearance hole or slotted hole or inclined to the perpendicular of the inner circumferential side of the clearance hole or slotted hole, and wherein the height of the through hole (the total height of the contact surface and the inner circumferential side) from the head part of the bone screw is not exceeded in all deflection positions of the connected head piece relative to the separate head piece.

The fact that the connected head piece does not protrude beyond the clearance hole or slotted hole into the interior of the implant (towards the side facing away from the patient's bone) in any deflection position with respect to the separate head piece ensures that an inlay provided in the implant does not rest on the head part of the bone screw.

Further preferably, the clearance hole of the separate head piece can be designed in such a way that in the assembled state of the head part, the connected head piece, in particular in all deflection positions relative to the separate head piece, is completely immersed in the clearance hole of the separate head piece.

Thereby it can be achieved in an advantageous way that the height of the head part (its length in the axial direction of the clearance hole) is not exceeded at the upper side of the separate head piece, in particular in all deflection positions of the connected head piece relative to the separate head piece. In the case of a plane upper side of the separate head piece, the proximal end of the bone screw is thus (always) plane in the assembled state of the head part, in particular in all deflection positions of the connected head piece relative to the separate head piece.

BRIEF DESCRIPTION OF THE DRAWING FIGURES

The invention is described in more detail below using preferred embodiments with reference to the attached drawings. These show:

The figures are merely schematic in nature and serve exclusively to understand the invention. The same elements are designated by the same reference signs.

DETAILED DESCRIPTION

Figure 1:
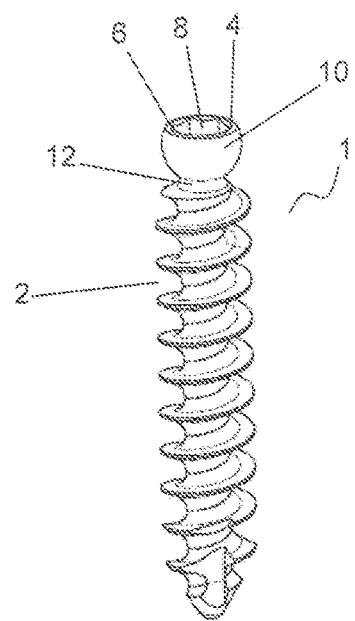
FIG. 1 shows a perspective view of a bone screw in a configuration of the invention.

FIG. 1 shows a medical bone screw 1 with a shaft-shaped thread part 2 and a rotationally symmetric head piece 4 connected in one piece with the thread part 2. The connected head piece 4 has a plane (axial) upper side 6 with a connection geometry 8 in the form of a hexagon embedded in the head piece 4 for interaction with an assembly tool. Alternatively, all other known connection geometries such as slots, cross slots or stars can be realized. Furthermore, the connected head piece 4 shows an outer circumferential side 10, which is convex towards the outside and has a larger diameter at the proximal end of the head piece 4 (at the circumferential outer edge of the upper side 6) than at the distal end of the head piece 4. The head piece 4 assumes a semi-spherical shape whose largest diameter lies between the proximal end of the head piece 4 and the distal end of the head piece 4. At the distal end of the head piece 4, a transition portion 12 is arranged, which connects the head piece 4 with the thread part 2. The transition portion 12 is threadless and has a diameter that is the same size as the core diameter of thread part 2. It is also possible that the diameter of the transition portion 12 is larger than the core diameter.

Figure 2:
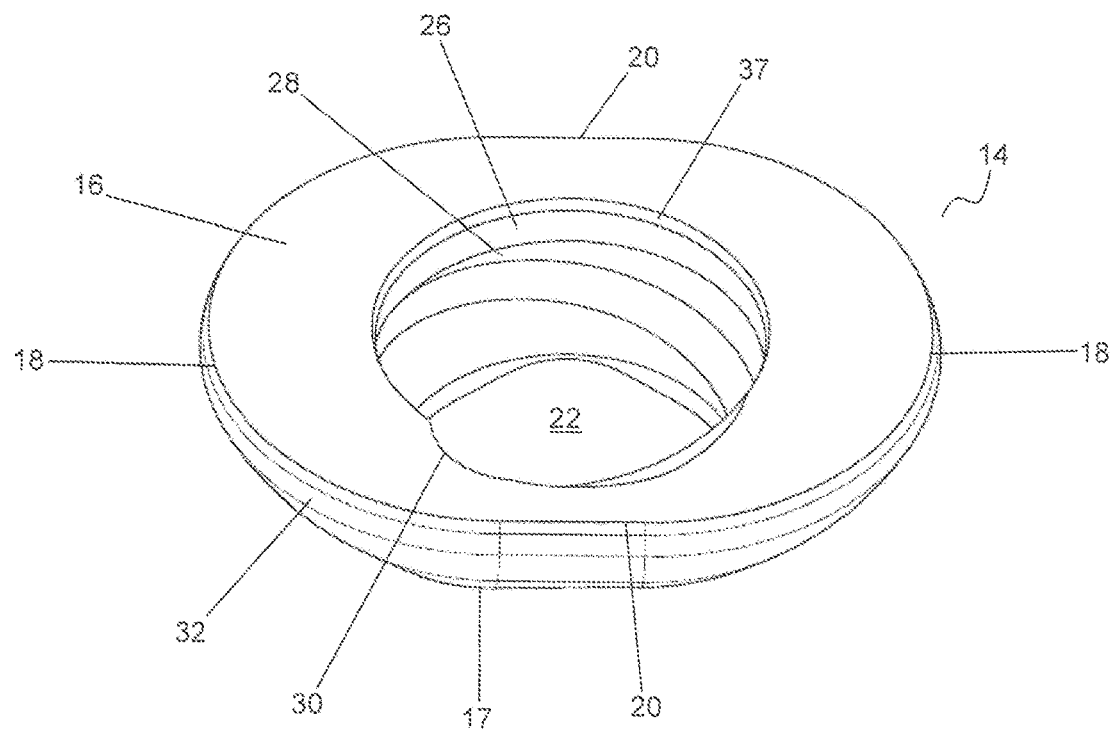
FIG. 2 shows a perspective view of a separate head piece in a configuration of the invention.

FIG. 2 shows a perspective view of a separate head piece 14. The separate head piece 14 has the geometrical shape of a plano-convex lens with a plane upper side 16 and furthermore has a plane lower side 17 which is essentially parallel to it. The plane upper side 16 of the separate head piece 14 assumes a substantially elliptical shape in plan view and has two opposite, circular or semicircular circumferential edges 18 and two opposite, substantially parallel circumferential edges 20. A clearance hole 22 runs through the plano-convex body of the separate head piece 14 from the center of the upper side 16 and extends substantially perpendicularly to the upper side 16 through the plano-convex body. The clearance hole 22 is rotationally symmetrical in shape and has a larger diameter at the common edge with the upper side 16 than at the common edge with the essentially flat lower side 17 of the separate head piece 14. The inner circumferential side 26 of the clearance hole 22 thus does not have a concave and/or essentially funnel-shaped form. The common edge of the clearance hole 22 with the upper side 16 has a circumferential chamfer 37. At the inner circumferential side 26, an inner thread 28 is cut into the plano-convex body of the head piece 14, which shows a recess 30 at the thread exit towards the upper side 16. The outer circumferential side 32 of the plano-convex body has a wider cross-section at the upper side 16 than at the lower side 17 in both the transverse and longitudinal direction of the head piece 14 and shows an overall convex shape.

The longitudinal direction of the head piece 14 is the direction of its longest extension in plan view and the transverse direction is the direction of its shortest extension in plan view.

Figure 3:
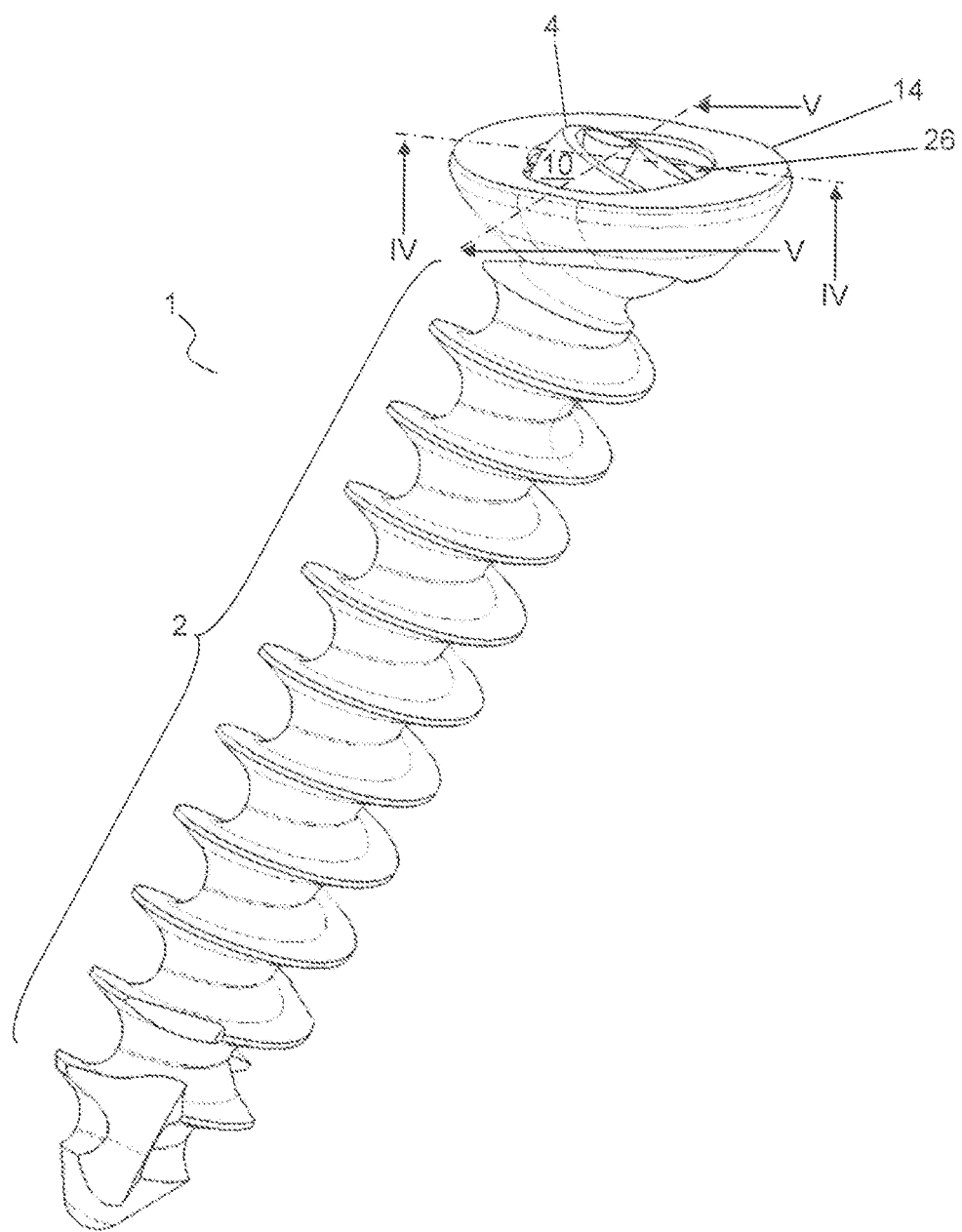
FIG. 3 shows a perspective view of an assembled bone screw in a configuration of the invention.

FIG. 3 shows a perspective view of a bone screw 1, in which the head piece 4 connected to the thread part 2 and the separate head piece 14 are assembled to form a head part 34. In the position shown, the outer circumferential side 10 of the connected head piece 4 is movably in contact with the inner circumferential side 26 of the separate head piece 14. In the assembly position, the head part assumes the function of a ball joint, in which the separate head piece 14 is formed in the manner of a ball socket and the head piece 4 in the manner of a joint, and the separate head piece 14 encloses the connected head piece 4 in such a way that a rotational movement of the two head pieces 4, 14 relative to each other is possible, but an axial movement of the two head pieces relative to each other is greatly limited or not possible. The dimension of the inner geometry of the head piece 14 is complementary to the outer geometry of the head piece 4. The assembly of the two head pieces 4, 14 is performed by screwing the thread part 2 into or through the separate head piece 14 until the thread part 2 has completely passed the separate head piece 14. The inner thread 28 (not visible) of the separate head piece 14 corresponds to the outer thread of the thread part 2.

Figure 4:
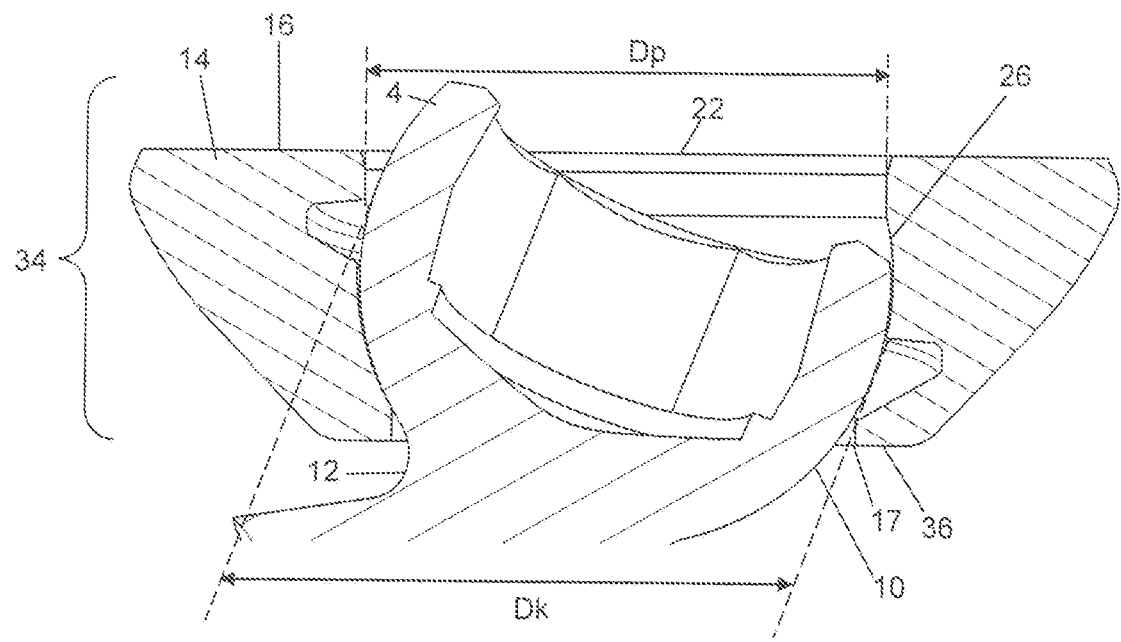
FIG. 4 shows a longitudinal section of the head part of the bone screw along line IV of FIG. 3.

FIG. 4 shows a longitudinal section of the head part 34 consisting of the separate head piece 14 and the connected head piece 4 along the line IV of FIG. 3. The connected head piece 4 is maximally deflected in relation to the separate head piece 14, i.e. the head piece 4 or the thread part 2 is in its maximum possible inclination position in relation to the lower side 17 (see left side of the figure). The common edge of the lower side 17 and the clearance hole 22 is in this inclination position on one side of the separate head piece 14 in the transition portion 12 and on the other side on the outer circumferential side 10 of the connected head piece 4. The complementary shape of the outer circumferential side 10 and the inner circumferential side 26 allows the head pieces 4, 14 to slide along each other and to be deflectable against each other, while the head pieces 4, 14 contact each other in an axially fixed manner. The lower side 17 has a flat surface section 36 between the clearance hole 22 and its circumferential outer edge. The clearance hole 22 has a proximal clearance-hole diameter Dp at its proximal end. The connected head piece 4 has an outer diameter Dk of the head piece. It can be seen that the proximal clearance-hole diameter Dp is narrower than the outer diameter Dk of the head piece. The proximal clearance-hole diameter Dp has a chamfer 37, the diameter of which increases towards the upper side 16, exceeding the proximal clearance-hole diameter Dp.

Figure 5:
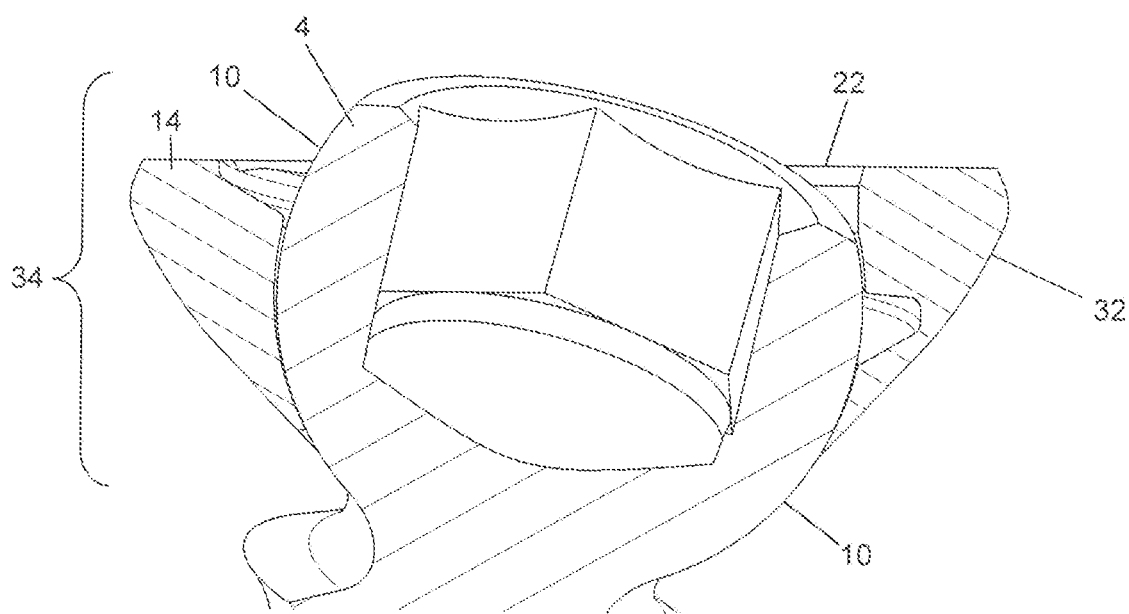
FIG. 5 shows a cross-section of the head part of the bone screw along line V of FIG. 3.

FIG. 5 shows a cross section of the head part 34 consisting of the separate head piece 14 and the connected head piece 4 along line V of FIG. 3. The connected head piece 4 is at its maximum deflection with respect to the separate head piece 14, i.e. the head piece 4 or thread part 2 is at its maximum possible inclination position with respect to the outer circumferential side 32 (see left side of the figure). In the transverse direction of the separate head piece 14, the clearance hole 22 and the outer circumferential side 32 of the separate head piece 14 form a common edge, against which the outer circumferential side 10 of the connected head piece 4 rests and moves along when the head pieces 4, 14 are deflected.

Figure 6:
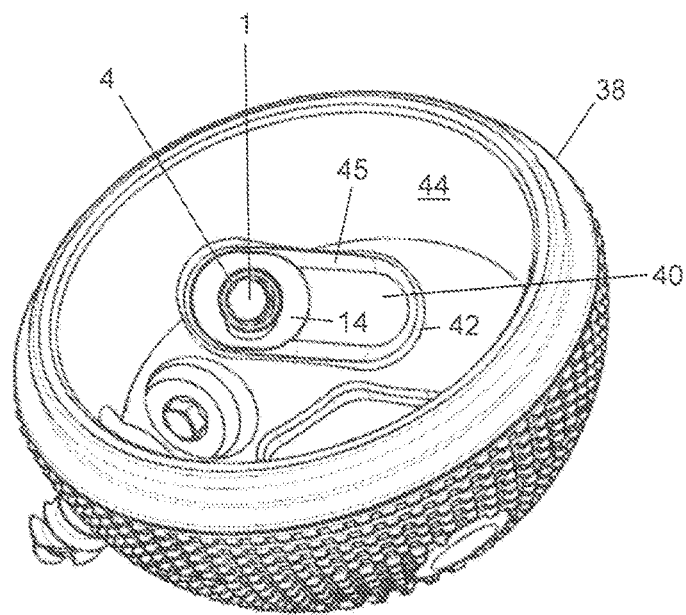
FIG. 6 shows a perspective interior view of an implant with a bone screw in a configuration of the invention.

FIG. 6 shows a perspective interior view of an implant 38 with a bone screw 1 in a configuration of the invention. The implant 38 is an acetabular implant, for example for use as a hip joint acetabular implant. At least one slotted hole 40 is introduced in the implant 38, the width of which (transverse to its longitudinal axis) is adapted to the diameter of the thread part 2 and to the transverse dimensions of the separate head piece 14. The slotted hole 40 has two opposite, parallel longitudinal sides along its longitudinal axis, two opposite, round transverse sides at its ends transverse to the longitudinal axis, and forms an inner circumferential side 42 along its inner circumference. The implant 38 has an inner side 44 through which a bone screw 1 can be inserted into the slotted hole 40.

The inner circumferential side 42 has at its proximal end a circumferential common edge with the inner side 44 and has at its distal end a circumferential contact surface 45, against which the separate head piece 14 rests or is supported. The contact surface 45 is inclined with respect to the inner circumferential side 42 and extends from the common edge with the inner circumferential side 42 towards the outside of the implant 38, thereby tapering the clearance hole 22. It can also be said that the diameter of the clearance hole 22 decreases (linearly and/or exponentially) both in the transverse and longitudinal direction of the slotted hole 40 along the contact surface 45 towards the outside of the implant 38.

The separate head piece 14 is in contact with the contact surface 45 and the inner circumferential side 42 in the assembled state shown and is therefore in surface contact with the implant 38 on its long sides and on one of its transverse sides. The total height of the inner circumferential side 42 and the contact surface 45, i.e. the distance between the inner side 44 and the outer side of the implant 38 in the direction of passage of the bone screw 1 through the slotted hole 40, is selected so that in the assembled state of the bone screw 1 with the implant 38, the head piece 34 (in all positions of the two head pieces 4, 14 relative to each other) does not protrude beyond the inner side 44, or the head piece 34 is completely countersunk in the slotted hole 40 in the assembled state of the bone screw 1 with the implant 38. The bone screw 1 can be positioned along the longitudinal axis of the slotted hole 40 depending on the desired entry position in the patient's bone.

The inner circumferential side 42 and/or the contact surface 45 of the slotted hole 40 is/are thereby formed on the transverse sides thereof complementary to the outer surfaces of the separate head piece 14 on the transverse sides thereof. Likewise, the inner circumferential side 42 and/or the contact surface 45 of the slotted hole 40 is/are formed on its longitudinal sides complementary to the outer surfaces of the separate head piece 14 on its longitudinal sides. Overall, the slotted hole 40 or the inner circumferential side 42 and the contact surface 45 thus assumes/assume a (substantially) trough-shaped or trough-like shape which is (at least partially) complementary to the outer circumferential side 32 of the separate head piece 14, so that the separate head piece 14 forms a surface contact at the contact surface 45 and/or at the inner circumferential side 42 of the slotted hole 40.

Figure 7:
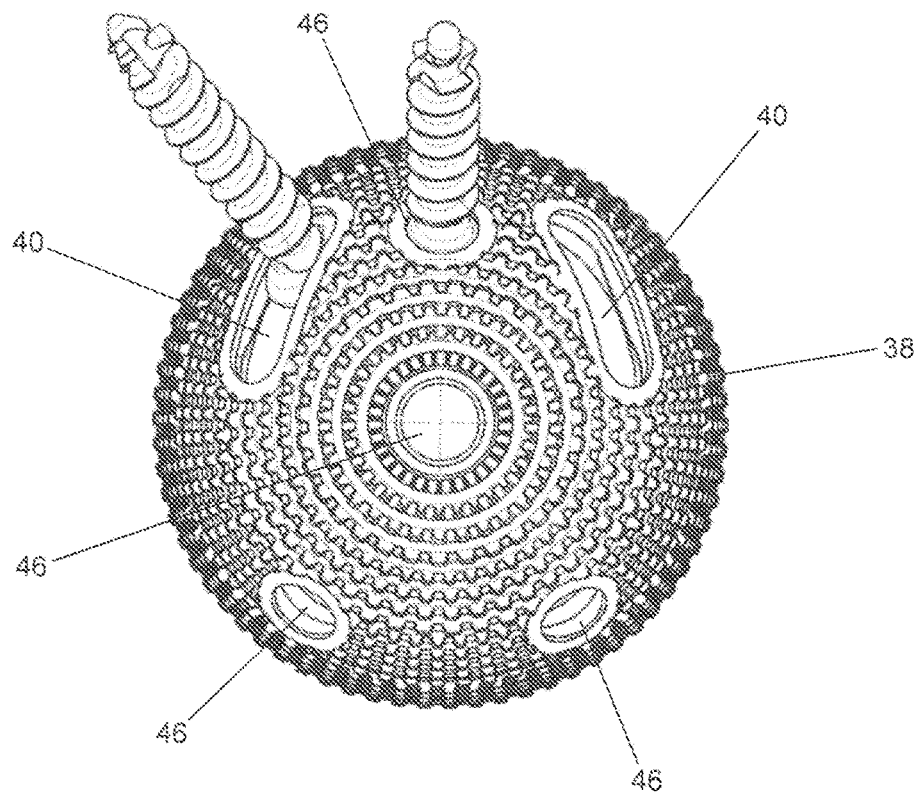
FIG. 7 shows a perspective external view of the implant of FIG. 6.

FIG. 7 shows a perspective exterior view of the implant of FIG. 6, showing that implant 38 has two slotted holes 40 and several round holes 46.

It is noted that instead of one slotted hole, a round clearance hole with the same properties may be provided. Instead of the longitudinal and transverse sides, a round clearance hole has equal radial sides. The separate head piece may have a substantially hemispherical shape with a flat, round upper side when viewed from above and a lower side that is substantially parallel to it. The round clearance hole may have a circumferential contact surface and/or an inner circumferential surface which is/are shaped complementary to the hemispherical shape of the separate head piece so that the separate head piece and the circumferential contact surface of the round clearance hole abut each other in the assembled state.

In other words, in summary, an implant system is stated having a hip-joint acetabular implant and a bone screw with articulated screw head, which allows an unchanged contact position of the screw head on the acetabular implant when the bone screw is oriented relative to the acetabular implant. For this purpose, the acetabular implant has a slotted hole in which the bone screw can be pivoted in longitudinal direction of the slotted hole.

The invention claimed is:
1. An implant system comprising at least a medical bone screw and a hip-joint acetabular implant having at least one first clearance hole through which the medical bone screw can be inserted in such a way that the medical bone screw can be pivoted at least in one direction of the at least one first clearance hole, wherein
  the medical bone screw has a shaft-shaped bone thread part for fastening the hip joint acetabular implant to a patient bone, which has a core diameter and an outer-thread diameter and at the proximal end of which a two-part, angle-adjustable head part is connected,
  the two-part, angle-adjustable head part is formed from a head piece, which is formed in one piece with the bone-thread part, which is preferably rotationally sym- metrical, more preferably partially spherical, and a head piece provided separately from the bone-thread part, the head piece provided separately from the bone-thread part has an upper side and a lower side, and a second clearance hole having an undercut or a funnel shape or tulip shape is formed therein, and the second clearance hole has a proximal clearance-hole diameter at the upper side and a distal clearance-hole diameter at the lower side, wherein the second clearance hole furthermore has an inner thread with an inner-thread diameter between the upper side and the lower side, the inner thread corresponding to the outer thread of the shaft-shaped bone-thread part, wherein the inner-thread diameter is greater than the outer-thread diameter and the distal clearance-hole diameter is greater than the core diameter, and by screwing the shaft-shaped bone thread part into the second clearance hole, the shaft-shaped bone-thread part is inserted into the head piece provided separately from the bone-thread part, in such a way that the head piece formed in one piece with the latter rests in an axially fixed manner on the undercut or in the funnel shape or tulip shape, but a pivoting movement of the shaft-shaped bone thread part with respect to the separate head piece is allowed in at least one or exclusively one pivoting plane.

2. The implant system according to claim 1, wherein the at least one first clearance hole is a slotted hole having two opposite, long longitudinal sides and two opposite, short transverse sides, wherein the medical bone screw is insertable in such a way through the slotted hole that the medical bone screw is pivotable at least in the longitudinal direction of the slotted hole.

3. The implant system according to claim 1, wherein the head piece formed in one piece with the bone-thread part has a head piece outer diameter and the second clearance hole has an intermediary clearance-hole diameter between the upper side and the lower side which is greater than, equal to, or smaller than the head piece outer diameter.

4. The implant system according to claim 1, wherein the proximal clearance-hole diameter is smaller than the head piece outer diameter.

5. The implant system according to claim 1, wherein the proximal clearance-hole diameter is larger than the distal clearance-hole diameter and/or the undercut or the funnel shape or tulip shape is designed and/or oriented such that an insertion direction of the shaft-shaped bone thread part from the upper side inevitably results.

6. The implant system according to claim 1, wherein the separate head piece in top view has a substantially elliptical shape with two opposite end portions with small radii and two opposite longitudinal portions with large radii, which are formed at least in longitudinal sections as parallel straight lines.

7. The implant system according to claim 1, wherein the separate head piece substantially assumes the shape of a plano-convex lens and that the upper side is planar.

8. The implant system according to claim 7, wherein the separate head piece formed as a substantially plano-convex lens has a flattening on its convex side which is oriented substantially plane-parallel to the planar upper side.

9. The implant system according to claim 1, wherein the bone screw has a threadless shaft portion arranged axially between the outer thread of the bone-thread part and the head piece formed in one piece therewith, said threadless shaft portion being dimensioned in such a way that the outer thread of the bone-thread part and the inner thread of the separate head piece are disengaged when the head piece, which is formed in one piece with the bone thread, lies in an axially fixed manner against the undercut or in the funnel shape or tulip shape.

10. The implant system according to claim 6, wherein the separate head piece establishes a line or surface supporting contact with the implant along the two opposite longitudinal portions with large radii.

11. The implant system according to claim 6, wherein the separate head piece can establish a line or surface supporting contact with the implant at one of the two opposite end portions with small radii.

12. The implant system according to claim 6, wherein at least one end portion with small radius of the separate head piece, preferably both end portions with small radii, is/are formed complementary to at least one transverse side of the at least one first clearance hole.

13. The implant system according to claim 1, wherein a circumferential contact edge is formed on an inner circumference of the at least one first clearance hole, on which the separate head piece is supported in such a way that the head piece formed in one piece with the bone thread does not project axially beyond the circumferential edge of the at least one first clearance hole.

* * * * *